United States Patent [19]

Dang et al.

[11] Patent Number: 5,531,710
[45] Date of Patent: Jul. 2, 1996

[54] COMBINATION CLOSURE AND SYRINGE

[75] Inventors: Nguyen T. Dang, Glendale; Lawrence B. Martin, Palmdale; Richard Jerrard, La Crescenta, all of Calif.

[73] Assignee: Courtaulds Aerospace, Inc., Burbank, Calif.

[21] Appl. No.: 393,860

[22] Filed: Feb. 24, 1995

[51] Int. Cl.⁶ .................................................. A61M 5/315
[52] U.S. Cl. ........................... 604/238; 215/355; 222/546; 604/256
[58] Field of Search ..................................... 215/307, 247, 215/355–357; 604/240, 241, 905, 192, 198, 110, 199, 256, 238; 222/546, 562, 563

[56] References Cited

U.S. PATENT DOCUMENTS

| | | | |
|---|---|---|---|
| 1,437,934 | 12/1922 | Fullerton | 604/238 X |
| 2,717,728 | 9/1955 | Gray | 222/546 |
| 3,118,578 | 1/1964 | Collins | 215/307 X |
| 3,318,496 | 5/1967 | Ayotte et al. | 215/307 X |
| 3,380,489 | 4/1968 | Harautuneian | 215/307 X |
| 3,606,107 | 9/1971 | Ardito et al. | 222/546 |
| 3,759,429 | 9/1973 | Ardito et al. | 222/546 |
| 4,133,462 | 1/1979 | Lindström | 222/546 |
| 4,213,546 | 7/1980 | Massey | 222/546 |
| 4,427,138 | 1/1984 | Heinlein | 222/546 |
| 4,516,697 | 5/1985 | Dreps et al. | 222/212 |
| 4,583,668 | 4/1986 | Maynard, Jr. | 215/390 X |
| 4,801,295 | 1/1989 | Spencer | 604/199 X |
| 5,328,474 | 7/1994 | Raines | 604/268 X |

FOREIGN PATENT DOCUMENTS

| | | |
|---|---|---|
| 45301 | 1/1953 | Australia. |
| 725024 | 3/1955 | United Kingdom. |
| 47903 | 3/1979 | United Kingdom. |

Primary Examiner—Allan N. Shoap
Assistant Examiner—Robin A. Hylton
Attorney, Agent, or Firm—Gifford, Krass, Groh, Sprinkle, Patmore, Anderson & Citkowski

[57] ABSTRACT

A closure is provided for a syringe of the type having a housing with a substantially tubular and cylindrical neck with a through bore through which the contents of the syringe are dispensed. The closure includes an elongated probe having a free end and a cross-sectional area substantially the same as the syringe through bore. The closure further includes a first and second tubular and cylindrical sealing ring. The first tubular and cylindrical ring has an inner diameter substantially the same as the outer diameter of the syringe neck while the second sealing ring is positioned concentrically around the first sealing ring. The sealing rings and probe are dimensioned so that, upon insertion of a free end of the probe into the syringe through bore, the probe and first sealing ring sealingly engage both the internal and external surfaces of the syringe neck. Simultaneously, the free ends of the first and second sealing ring sealingly engage the outer surface of the syringe housing. Additionally, the closure includes a base plate which is substantially perpendicular to the longitudinal axis of the probe and sealing rings. With the closure positioned on the syringe, the base plate enables the syringe to be stored vertically on end.

9 Claims, 1 Drawing Sheet

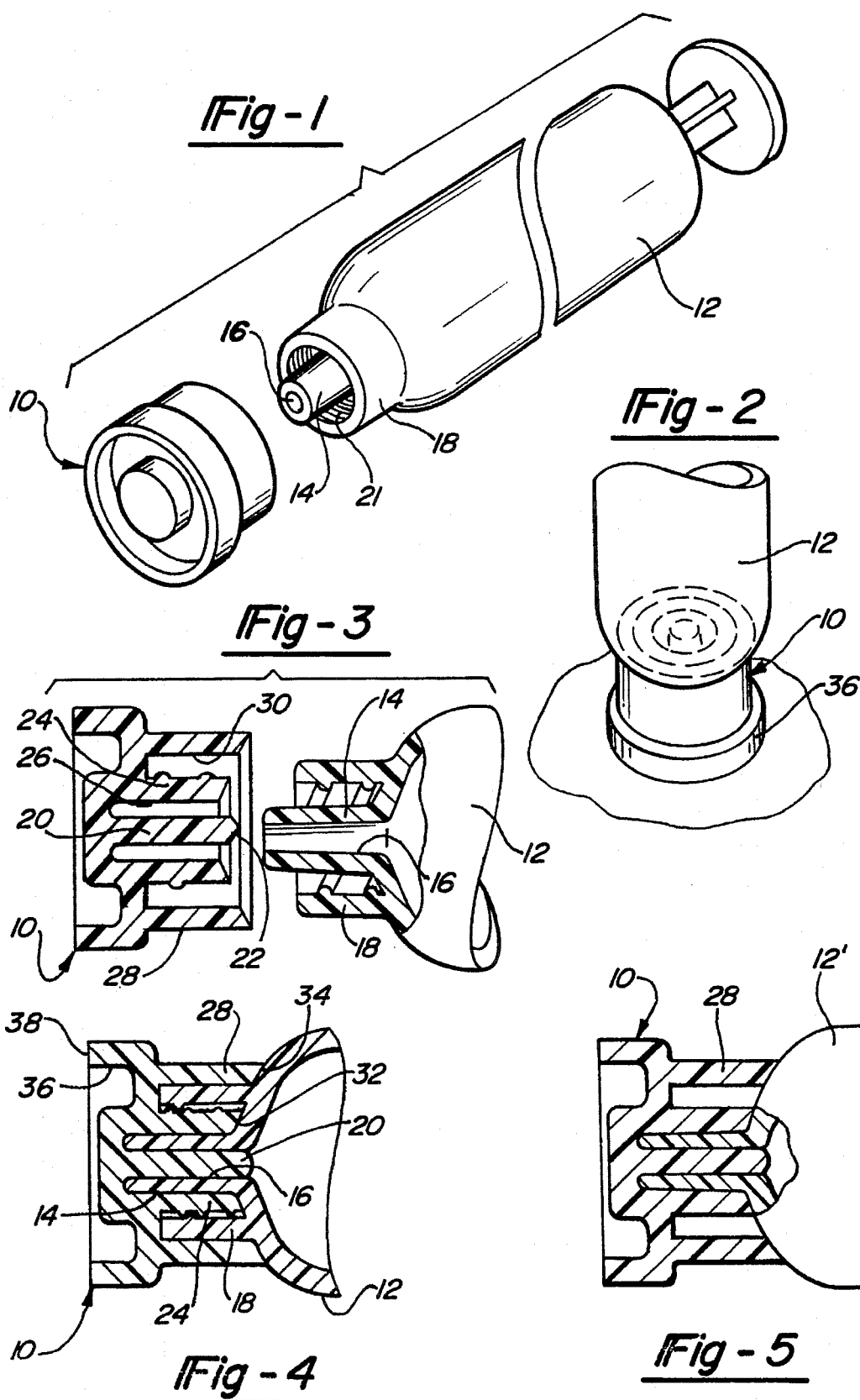

COMBINATION CLOSURE AND SYRINGE

BACKGROUND OF THE INVENTION

I. Field of the Invention

The present invention relates generally to closures and, more particularly, to a closure for a syringe.

II. Description of the Prior Art

Syringes are commonly used not only for medical applications, but also in non-medical applications, such as glue dispensers and the like. Such syringes typically comprise an elongated housing having a tubular neck at one end. A needle or dispensing tip is typically attached to the syringe neck so that the contents of the syringe are dispensed out through the tip or needle. In high pressure applications, the dispensing tip or needle is typically threadably secured to an attachment collar disposed concentrically around the syringe neck whereas a friction or slide fit is oftentimes adequate for low pressure dispensing applications.

Prior to attachment of the syringe needle or dispensing tip, e.g. when the syringe is shipped or stored, it has been previously known to attach a cap to the syringe tip to prevent leakage of the contents of the syringe. These previously known caps, however, have suffered from a number of disadvantages.

One disadvantage of these previously known caps or closures is that the closure fails to maintain an adequate seal with the syringe. Such failure results in leakage of the contents of the syringe during shipping or storage.

A still further disadvantage of these previously known closures is that the closures are relatively small and difficult to manually remove from the syringe. In some cases, it is necessary to use pliers or other tools to remove the tip which can result in damage to the syringe neck. Such damage, in turn, can result in an inadequate seal between the dispensing needle or dispensing tip once attached to the syringe.

A still further disadvantage of the previously known closures for syringes is that such closures fail to protect the syringe from breakage of the syringe neck and/or attachment collar. Breakage of the syringe neck or attachment collar, of course, requires that the syringe be discarded.

A still further disadvantage of these previously known closures for syringes is that such closures do not enable the syringe to be stored vertically on end. As such, these previously known syringes were frequently stored on their side on a bench thus taking up excessive bench space.

SUMMARY OF THE PRESENT INVENTION

The present invention provides a closure for a syringe which overcomes all of the above-mentioned disadvantages of the previously known devices.

In brief, the closure of the present invention comprises an elongated probe having a free end and a cross-sectional area substantially the same as the area of the syringe through bore. A first tubular and cylindrical sealing ring is provided concentrically around the probe. Additionally, the first sealing ring has a free end and an inner diameter substantially the same as the outer diameter of the syringe neck. Thus, upon insertion of the probe into the syringe through bore, the probe seals the inner surface of the syringe neck while, simultaneously, the first sealing ring sealingly engages the outer surface of the syringe neck.

The closure further includes a second tubular and cylindrical sealing ring provided concentrically around the first sealing ring. The second sealing ring, like the first ring, has a free end which sealingly engages the outer surface of the syringe once the closure is positioned onto the syringe. Additionally, the second sealing ring is dimensioned to fit around the attachment collar, if present and protects the attachment collar from contaminates, as well as from damage through impact.

In the preferred embodiment of the invention, the closure includes a base plate which faces outwardly from the syringe. The base plate includes a surface generally perpendicular to the axis of the syringe neck and enables the syringe to be stored vertically on end.

In the preferred embodiment of the invention, the probe, sealing rings and base plate are of a one piece, thermoplastic construction.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is an exploded view illustrating a preferred embodiment of the present invention;

FIG. 2 is a fragmentary elevational view illustrating the syringe in a storage position;

FIG. 3 is an exploded longitudinal sectional view illustrating the closure in preparation for attachment to the syringe;

FIG. 4 is a longitudinal sectional view illustrating the closure attached to the syringe and in a sealing position; and FIG. 5 is a view similar to FIG. 4 but illustrating the use of the closure of the present invention with a different type of syringe.

DETAILED DESCRIPTION OF A PREFERRED EMBODIMENT OF THE PRESENT INVENTION

With reference first to FIG. 1, an illustration of a preferred embodiment of the closure 10 of the present invention is thereshown for use with a syringe 12. The syringe 12 is elongated and generally cylindrical in shape having a tubular and cylindrical neck 14 at one end. The neck 14 includes a longitudinal through bore 16 through which the contents of the syringe 12 are dispensed. Additionally, a tubular and cylindrical attachment collar 18 is provided concentrically around the neck 14. This attachment collar 18 may be internally threaded, as shown at 21, for attachment with a dispensing tip or needle (not shown).

With reference now particularly to FIG. 3, the closure 10 is thereshown in greater detail and includes an elongated probe 20 having substantially the same, or slightly larger, cross-sectional shape and area as the neck through bore 16. Conventionally, both the probe 20 and through bore 16 are cylindrical in cross-sectional shape. Additionally, a free end 22 of the probe 20 is preferably tapered to facilitate insertion of the probe 20 into the through bore 16.

A first tubular and cylindrical sealing ring 24 is provided concentrically around the probe 20. The first sealing ring has an internal bore 26 with substantially the same, or slightly smaller, diameter as the outside diameter of the syringe neck 14. Thus, with the first sealing ring 24 positioned around the syringe neck 14, the sealing ring 24 sealingly engages the outer surface of the neck 14.

Still referring to FIG. 3, the closure 10 further includes a second tubular and cylindrical sealing ring 28 which is positioned concentrically around and spaced from the first sealing ring 24. The second sealing ring 28 has an internal bore 30 with a diameter substantially the same as the outside diameter of the attachment collar 18.

With reference now particularly to FIG. 4, the closure 10 is there illustrated attached to the syringe 12. With the closure 10 attached to the syringe 12, the probe 20 sealingly engages the internal surface of the syringe through bore 16. Simultaneously, the first sealing ring 24 sealingly engages the outer surface of the syringe neck 14 while the outer sealing ring 28 encloses the attachment collar 18 thus protecting collar 18 not only from contaminants, but also from damage due to impact.

Still referring to FIG. 4, the free ends 32 and 34 of the first and second sealing rings 24 and 28, respectively, are shaped so that they flatly abut against the outer surface of the syringe 12. This flat abutment further enhances the seal between the sealing rings 28 and 24 and the syringe 12.

With reference now particularly to FIGS. 2 and 4, the closure 10 includes a cylindrical base plate 36 which faces away from the syringe 12 and has a diameter greater than the diameter of the outer sealing ring 28. The base plate 36 includes an annular flat surface 38 which lies in a plane generally perpendicular to the longitudinal axis of the syringe neck 14. As such, the base plate 36 enables the syringe to be stored vertically on end, as illustrated in FIG. 2, which not only minimizes bench space consumed by the syringe 12 prior to use, but also facilitates filling of the syringe 12. As best shown in FIG. 4, the annular flat surface 38 of the base plate 36 encloses an area of the base plate which is axially recessed, i.e. does not protrude outwardly from, the annular flat surface 38.

With reference now to FIG. 5, a different type of syringe 12' is there illustrated in which the attachment collar 18 (FIG. 1) is omitted. Such syringes are typically utilized in low pressure applications where a friction or slide fit dispenser tip is used with the syringe 12'. As shown in FIG. 5, the closure 10 can also be utilized without modification with this type of syringe 12'. Furthermore, as shown in FIG. 5, the second sealing ring 28 of the closure 10 provides an additional sealing surface on the syringe 12'.

The probe 20, sealing rings 24 and 28 and base plate 36 are preferably of a one piece construction. Furthermore, preferably the entire closure is molded from a thermoplastic material.

Having described my invention, it can be seen that the closure of the present invention provides a simple and yet highly effective closure for a syringe which not only eliminates leakage of the contents of the syringe, but also protects the syringe neck and attachment collar, if present, from damage. The closure also enables the syringe to be stored on end in a vertical position which not only facilitates shipping and storage, but also filling of the syringe.

Having described my invention, however, many modifications thereto will become apparent to those skilled in the art to which it pertains without deviation from the spirit of the invention as defined by the scope of the appended claims.

We claim:

1. In combination, a syringe and a closure for said syringe of the type having a housing with a substantially tubular cylindrical neck, said neck having a longitudinal through bore through which contents of the syringe are dispensed, said closure comprising:

an elongated probe having a free end and a cross sectional area substantially the same as the syringe through bore, a first tubular and cylindrical sealing ring, said first sealing ring having a free end and an inner diameter substantially the same as an outer diameter of the syringe neck, a second tubular and cylindrical sealing ring, said second sealing ring having a free end and positioned concentrically around said first sealing ring, wherein said sealing rings and probe are dimensioned so that, with said probe inserted into the syringe through bore, said free ends of said sealing rings sealingly engage an outer surface of the syringe housing while said probe and said first sealing ring respectively continuously sealingly engage an internal surface and external surface of the syringe neck along the entire length and circumference of said probe and said first sealing ring, wherein said closure further comprises a base plate, said base plate having a flat surface substantially perpendicular to a longitudinal axis of said probe, said base plate being attached to the ends of said probe and sealing rings opposite from said free ends, said base plate having a cross-section greater in size than the cross-sectional shape of the second sealing ring, said base plate having an axial end facing away from said syringe, said axial end of said base plate having an annular flat surface about its outer periphery, said annular flat surface lying in a plane perpendicular to the axis of the syringe neck, and wherein an area of said base plate end enclosed by said base plate planar surface is axially recessed from said base plate planar surface.

2. The invention as defined in claim 1 wherein said free ends of said sealing rings flatly abut against the outer surface of the syringe housing.

3. The invention as defined in claim 1 wherein said probe and said sealing rings are of a one piece construction.

4. The invention as defined in claim 3 wherein said probe and said sealing rings are constructed of a thermoplastic material.

5. The invention as defined in claim 1 wherein said probe, said sealing rings and said base plate are of a one piece construction.

6. The invention as defined in claim 1 wherein said base plate is cylindrical in shape.

7. The invention as defined in claim 6 wherein said base plate has a diameter greater than said second sealing ring.

8. The invention as defined in claim 6 wherein said base plate is tubular in shape.

9. The invention as defined in claim 1 wherein the syringe includes an annular attachment collar positioned concentrically around and spaced from the neck and wherein an internal diameter of said second sealing ring is substantially the same as an outer diameter of the attachment collar.

* * * * *